United States Patent
Longobardo et al.

[11] Patent Number: 5,921,941
[45] Date of Patent: Jul. 13, 1999

[54] DISPOSABLE STETHOSCOPE COVER

[76] Inventors: John J. Longobardo; Sherri A. Longobardo, both of 3095 Point Clear Dr., Tega Cay, S.C. 29715; Thomas J. Bower, 11 Sandy Cove La., Lake Wylie, S.C. 29710

[21] Appl. No.: 09/118,529

[22] Filed: Jul. 17, 1998

[51] Int. Cl.⁶ .................................................. A61B 7/02
[52] U.S. Cl. ................................................ 600/528
[58] Field of Search ............................... D24/105, 134, D24/141; 181/131, 137; 600/528; 128/844, 918; 381/67

[56] References Cited

U.S. PATENT DOCUMENTS

| | | |
|---|---|---|
| 2,358,440 | 9/1944 | Bowman . |
| 4,032,687 | 6/1977 | Hornsby, Jr. . |
| 4,206,844 | 6/1980 | Thukamoto et al. . |
| 4,820,290 | 4/1989 | Yahr . |
| 4,867,265 | 9/1989 | Wright . |
| 4,995,473 | 2/1991 | Packard . |
| 5,365,023 | 11/1994 | Lawton ................................ 600/528 |
| 5,366,776 | 11/1994 | Mertens . |
| 5,418,022 | 5/1995 | Anderson et al. . |
| 5,428,193 | 6/1995 | Mandiberg . |
| 5,823,191 | 10/1998 | Cho .................................... 128/844 |

FOREIGN PATENT DOCUMENTS

37211348 A1  1/1989  Germany .

OTHER PUBLICATIONS

Express Physicians Supply Corporation (catalog); "Scope-Shield" by Labtron; Published prior to Jul. 17, 1998.

Primary Examiner—William E. Kamm
Assistant Examiner—George R. Evanisko
Attorney, Agent, or Firm—Adams Law Firm, P.A.

[57] ABSTRACT

A disposable cover for a stethoscope for being placed in a tensioned condition over and covering a patient-contacting portion of the stethoscope. The cover includes an elastomeric material defining a disc-shaped body, a raised rim integrally-formed with and surrounding the body, and a centrally-disposed, raised dimple integrally-formed in the body for being grasped and pulled away from the stethoscope when removal of the cover from the stethoscope is desired. The cover may include perforations or some other form of weakness area which tear the cover to facilitate removal when desired.

8 Claims, 9 Drawing Sheets

DISPOSABLE STETHOSCOPE COVER

TECHNICAL FIELD AND BACKGROUND OF THE INVENTION

This invention relates to a disposable cover for a stethoscope. The cover prevents direct contact between the stethoscope and the patient, and minimizes the possibility of the transfer of infection from one patient to another. In addition, the cover avoids patient discomfort which may be caused by placement of the metal bell or the flat diaphragm of a stethoscope against bare skin.

Cross-transmission of body fluids has become an increasingly serious problem in the past decade. The obvious and highly-publicized problem of preventing transmission of HIV infection has resulted in numerous additional measures intended to protect both patients and health care providers. These requirements include face shields, rubber gloves, hazardous material disposal devices, syringes designed to prevent or minimize the possibility of needle-sticks, and many others. Despite the existence of several prior art patents disclosing stethoscope covers and the commercial availability of at least one stethoscope cover, they are seldom used. Yet health care providers uniformly monitor pulse rate, breath sounds and heart function in environments, such as emergency rooms, where some level of cross-contamination of patients by blood, mucus and/or other body excreta is almost certain. Many types of dermatological conditions may also be transmitted by cross-contamination of medical devices such as stethoscopes.

The disposable cover according to this application is sufficiently inexpensive that cost is negligible and is easy to apply and remove with one hand. No dispenser is required. Rather, a large number can be carried in, for example, a lab coat pocket where they are readily accessible. They can be discarded after one use in exactly the same manner as disposable examination gloves.

The prior art discloses a cover for a stethoscope which comprises a fabric which is gathered with an elasticized hem into a cup-shaped cover which can be fitted over the bell of the stethoscope. See, U.S. Pat. No. 5,269,314.

The prior art also discloses a diaphragm cover for a stethoscope. The cover is a flexible, resilient, imperforate membrane sheet with a rigid rim with two locking tabs which clip over the outer edge of the bell of the stethoscope. See, U.S. Pat. No. 4,461,368.

Other prior art patents include U.S. Pat. Nos. 5,428,193, 4,032,687, 4,867,265, and German Patent No. 3721348.

Labtron, the diagnostic division of Graham-Field sells a stethoscope cover under the trademark "Scopeshield", which comprises a flat, imperforate sheet packaged in a dispenser box. Each sheet has an adhesive coating on one side protected by a removable backing until use. The sheet is placed on and adheres only to the rim of the bell or diaphragm of the stethoscope. Thus, areas of the stethoscope other than the bell or diaphragm remain uncovered and thus unprotected. Moreover, traces of adhesive from the cover may cling to the stethoscope upon removal and accumulate over time. Such adhesive may actually facilitate accumulation of infectious material on the stethoscope.

SUMMARY OF THE INVENTION

Therefore, it is an object of the invention to provide a disposable stethoscope cover which is inexpensive.

It is another object of the invention to provide a disposable stethoscope cover which prevents direct contact between the stethoscope and the patient and minimizes the possibility of the transfer of infection from one patient to another.

It is another object of the invention to provide a disposable stethoscope cover which promotes aseptic contact between the health provider and patient.

It is another object of the invention to provide a disposable stethoscope cover which prevents discomfort which may be caused by placement of a bare metal stethoscope bell or diaphragm against bare skin.

It is another object of the invention to provide a disposable stethoscope cover which is it easily disposed of.

It is another object of the invention to provide a disposable stethoscope cover which can be placed on and removed from the stethoscope with one hand.

It is another object of the invention to provide a disposable stethoscope cover which does not require a dispenser.

It is another object of the invention to provide a disposable stethoscope cover which covers both the rim of the bell or diaphragm and surrounding structural parts of the stethoscope.

It is another object of the invention to provide a disposable stethoscope cover which does not require other disposable waste such as a backing sheet, dispenser or enclosure.

It is another object of the invention to provide a disposable stethoscope cover which avoids the need to attempt frequent sterilization or disinfection of the patient-contacting portions of the stethoscope.

It is another object of the invention to provide a disposable stethoscope cover which has the ability to be autoclaved and packaged sterile. A sterile device allows for the use of a stethoscope in a sterile environment/field.

It is another object of the invention to provide a disposable stethoscope cover which avoids possible accumulation of adhesive on the stethoscope.

These and other objects of the present invention are achieved in the preferred embodiments disclosed below by providing a disposable cover for a stethoscope for being placed in a tensioned condition over and covering a patient-contacting portion of the stethoscope. The cover comprises an elastomeric material defining a disc-shaped body, a raised rim integrally-formed with and surrounding the body, and a centrally-disposed, raised dimple integrally-formed in the body for being grasped and pulled away from the stethoscope when removal of the cover from the stethoscope is desired.

Preferably, the cover is generally round or elliptical in overall shape, and has a diameter which is less than the diameter of the patient-contacting portion of the stethoscope.

According to one preferred embodiment of the invention, the cover includes a weakness area for being easily torn which the cover is stretched during removal of the cover from the stethoscope.

Preferably, the weakness area comprises a line of perforations in the rim of the cover.

According to another preferred embodiment of the invention, the weakness area comprises a line of axially-extending perforations in the rim of the cover.

According to yet another preferred embodiment of the invention, the weakness area comprises two lines of perforations in opposed circumferential sides of the rim of the cover.

According to yet another preferred embodiment of the invention, the elastomeric material is chosen from a group consisting of latex rubber, synthetic rubber, polyurethane and vinyl.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
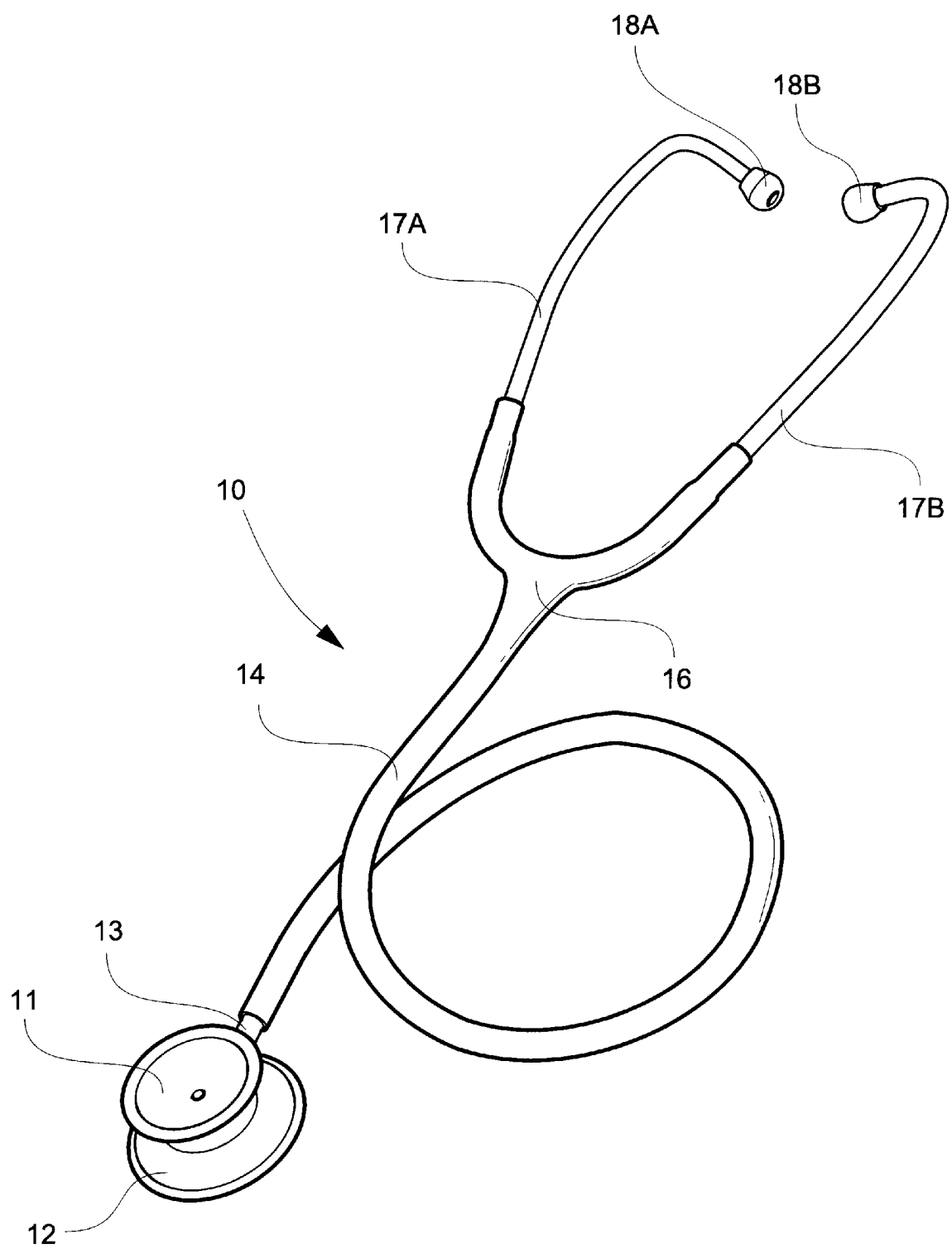
FIG. 1 is a perspective view of a conventional stethoscope on which a cover according to an embodiment of the invention may be used.

Referring now specifically to the drawings, a stethoscope of a type with which a stethoscope cover according to the present invention may be used is illustrated in FIG. 1 and shown generally at reference numeral 10. The stethoscope shown is the type manufactured by Minnesota Mining and Manufacturing Company and referred to as a "Littmann" stethoscope. The stethoscope 10 includes a sound receiving chestpiece which may include both a bell 11 and an opposed diaphragm 12. The bell 11 and the diaphragm 12 are sometimes collectively referred to as the "chestpiece."

The bell 11 and diaphragm 12 are integrally-formed and connect by means of a tubular to fitting 13 to a flexible tube 14 which includes a yoke 16. Ear tubes 17A and 17B are connected to the tube 14 through the yoke 16 and include eartips 18A and 18B which are received in the ears of the user. The frequencies detected and amplified by the bell 11 or the diaphragm 12 are transmitted through the tube 14 and the ear tubes 17A, 17B to the eartips 18A, 18B. The bell 11 and the diaphragm 12 comprise the patient-contacting portions of the stethoscope 10 and are the portions which should be covered and protected against contact with body fluids, tissue and skin.

Other stethoscope types, such as a Littmann Cardiology stethoscope, include a bell mode and diaphragm mode incorporated into a single side. See, U.S. Pat. No. 4,995,473. Other stethoscopes on which the invention according to the invention may be used include those made by Tycos and Graham-Field, among others.

Figure 2:
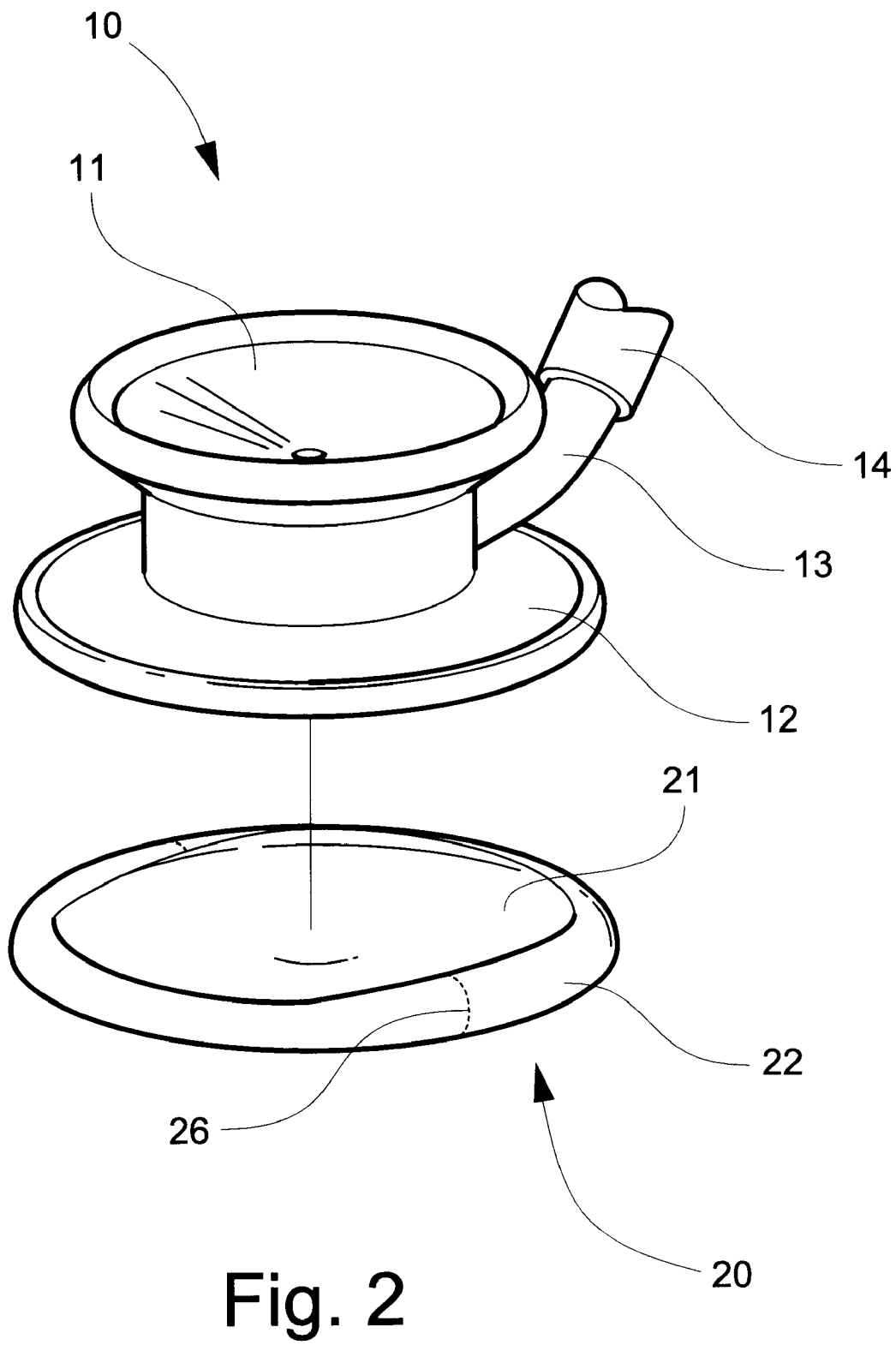
FIG. 2 is a fragmentary perspective view of the disposable stethoscope cover being placed on a stethoscope such as shown in FIG. 1.

Referring now to FIG. 2, a stethoscope cover 20 according to an embodiment of the invention is shown being placed on the diaphragm 12 of the stethoscope 10. Stethoscope cover 20 is preferably formed of latex rubber of the type used to fabricate latex examination gloves. Other materials from which the stethoscope cover 20 may be fabricated include synthetic rubber, polyurethane or vinyl. The stethoscope cover 20 may be powder-coated nor non-powder-coated, textured or non-textured, and hypo-allergenic or non-hypo-allergenic. As used herein, the term "elastomeric" is intended to include any relatively stretchable, membrane-like material such as examination gloves are made or could be made from.

Figure 5:
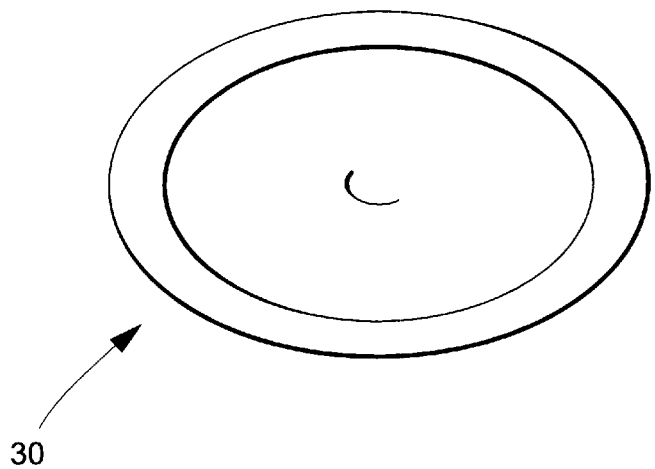
FIG. 5 is a plain view elevation of a disposable stethoscope cover according to another embodiment of the invention, showing an elliptical version of the cover.

As is shown in FIG. 2, the stethoscope cover 20 is formed of a disc-shaped body 21 with an annular, integrally-formed, raised rim 21 which extends around the circumference of the body 21 and curls inwardly toward the center. The stethoscope cover 20 is preferably undersized by approximately 10–20 percent in relation to the structure over which it will be placed to facilitate it being held in position on the stethoscope 10 in a taut condition. Alternatively, the cover may be elongated along one axis to facilitate placement of the cover on the stethoscope. See cover 30 at FIG. 5.

Preferably, the cover 20 is fabricated of latex between 2 and 6 mils thick, although other thicknesses may be appropriate. Thicknesses within the specified range have no appreciable effect on the acoustic transmission efficiency of conventional stethoscopes.

Figure 3:
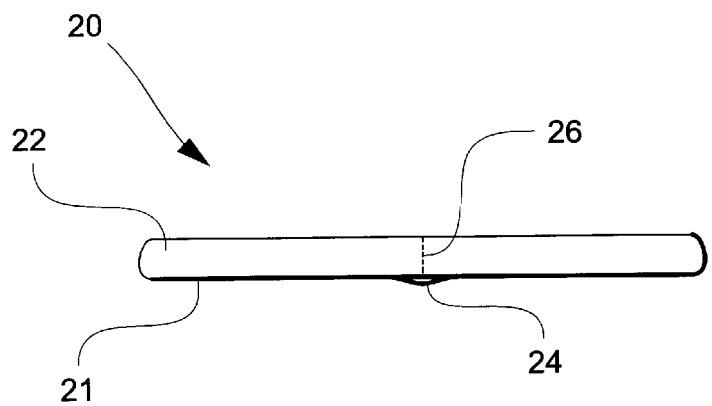
FIG. 3 is a side elevation a disposable stethoscope cover according to one preferred embodiment of the invention.
Figure 4:
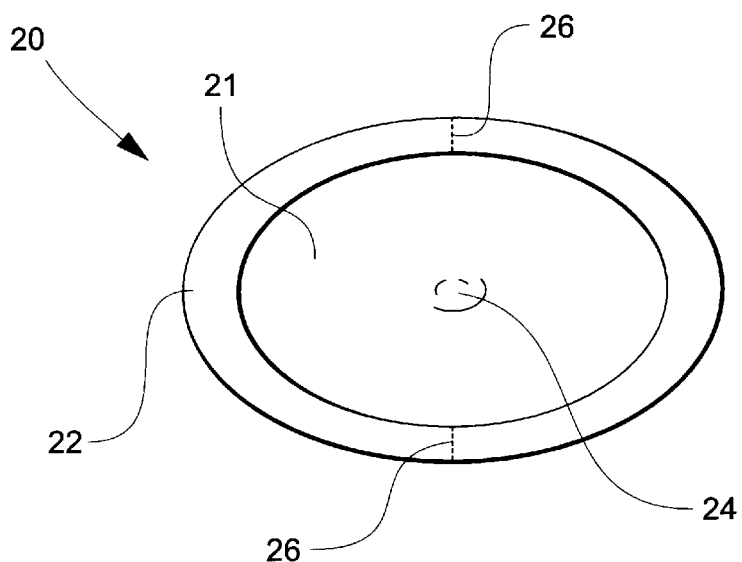
FIG. 4 is a perspective view of the disposable stethoscope cover shown in FIG. 3.

As is shown in FIGS. 3 and 4, stethoscope cover 20 includes a centrally disposed, outwardly-extending dimple 24. This dimple 24 permits the cover 20 to be quickly and easily grasped and removed with one hand from the stethoscope 10 by the user. Removal of the cover 20 is facilitated by the provision of at least one weakness area in the rim 22. This weakness area may be an axially-extending line of perforations 26, as shown in the drawings, or may be a narrow, axially-extending area of thinner material. In either instance, the weakness area is intended to tear when the cover 20 is grasped by the dimple 24 and pulled away from the bell of the stethoscope 10, as described further below. The perforations 26 are normally closed when the cover 20 is in its relaxed condition prior to placement on the stethoscope 10, and when the cover 20 is in a tensioned condition on the stethoscope 10. Thus, the perforations 26 will not pass liquids while the cover 20 is in use.

Figure 6:
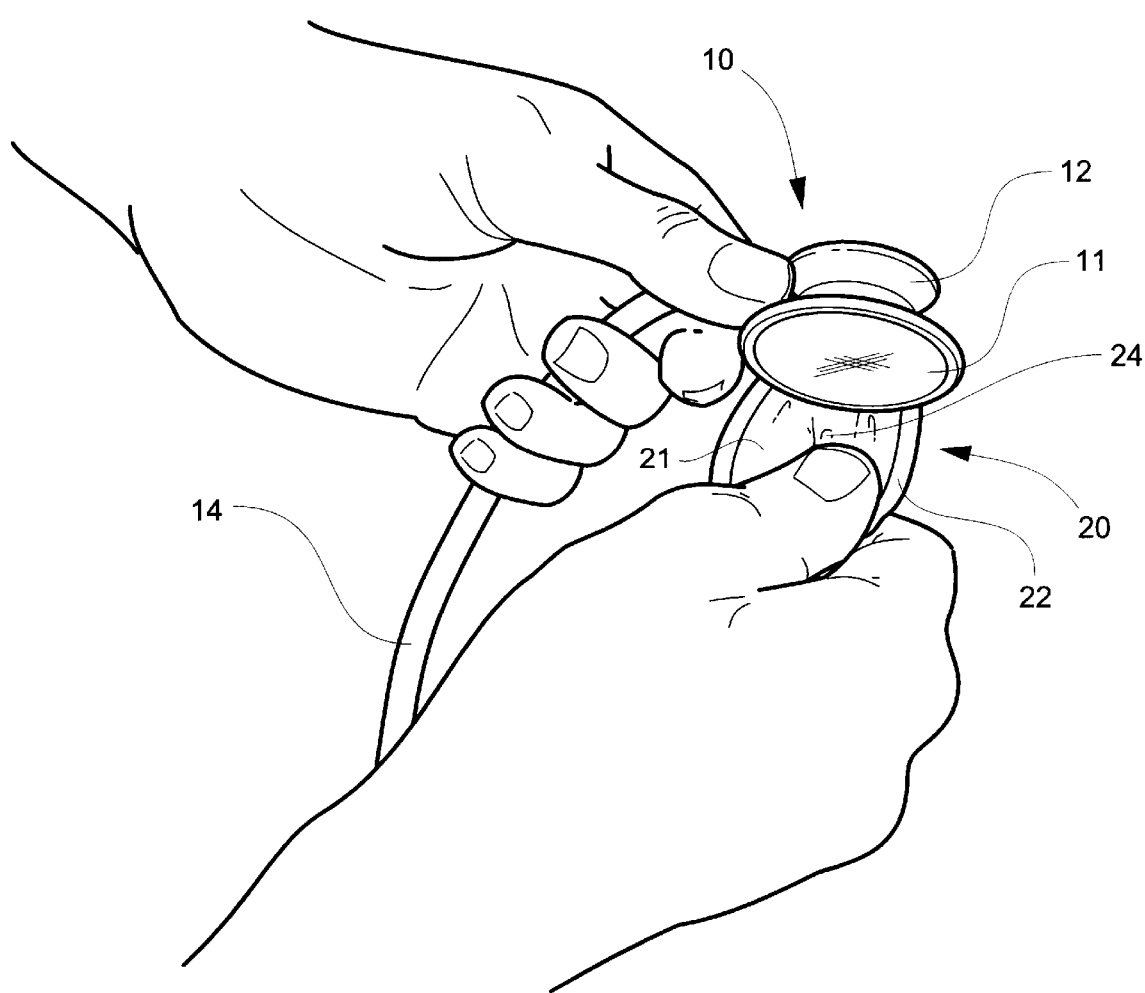
FIG. 6 is a perspective view showing placement of a stethoscope cover according to the invention onto a stethoscope.

Referring now to FIG. 6, placement of the stethoscope cover 20 onto the stethoscope 10 is explained in further detail. As noted above, the cover 20 needs no dispenser, individual packaging or disposable backings. They may be sold and dispensed from boxes in the same manner as latex examination gloves. A dispensing box the same size as one in which 100 latex gloves are sold will hold approximately 1000 covers 20. The covers 20 are simply packed into a dispensing box and then removed as needed. A handful can be removed at one time and placed in some other convenient place, such as the pocket of a lab coat where they can be easily and quickly retrieved when needed by the stethoscope user.

Figure 7:
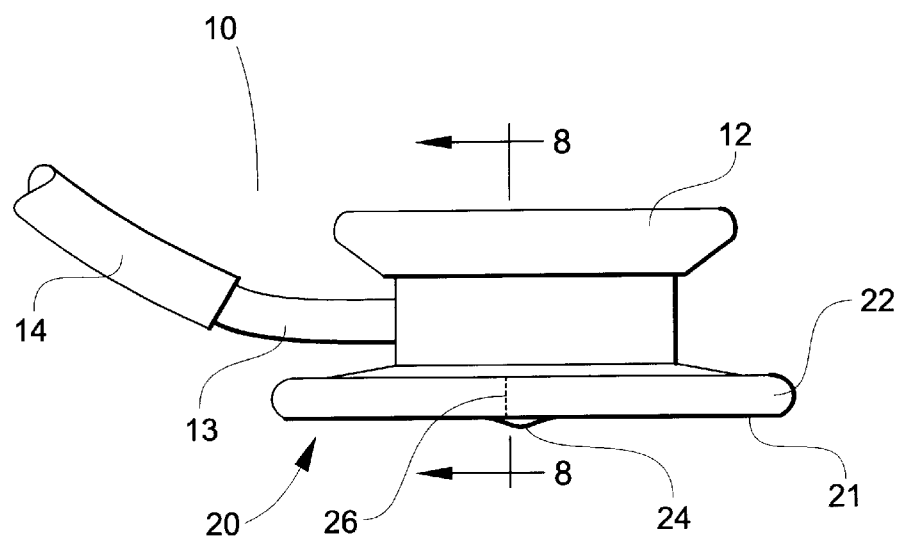
FIG. 7 is a side elevation of the stethoscope in place on a stethoscope.
Figure 8:
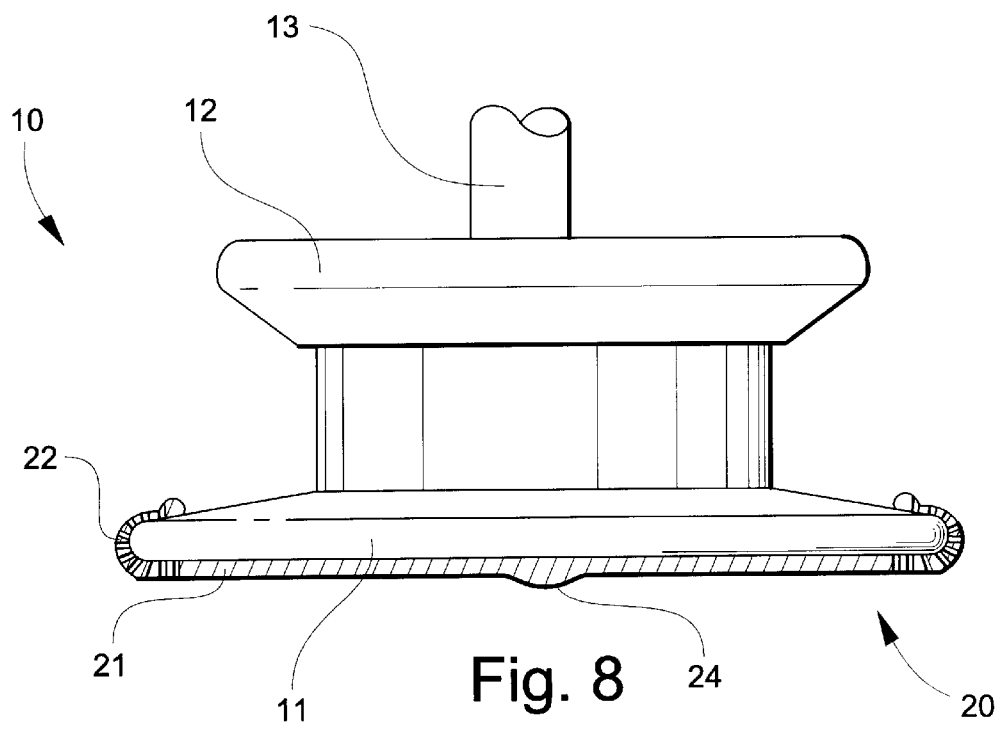
FIG. 8 is an enlarged, partial cross-sectional view showing the stethoscope cover in place on a stethoscope.
Figure 9A:
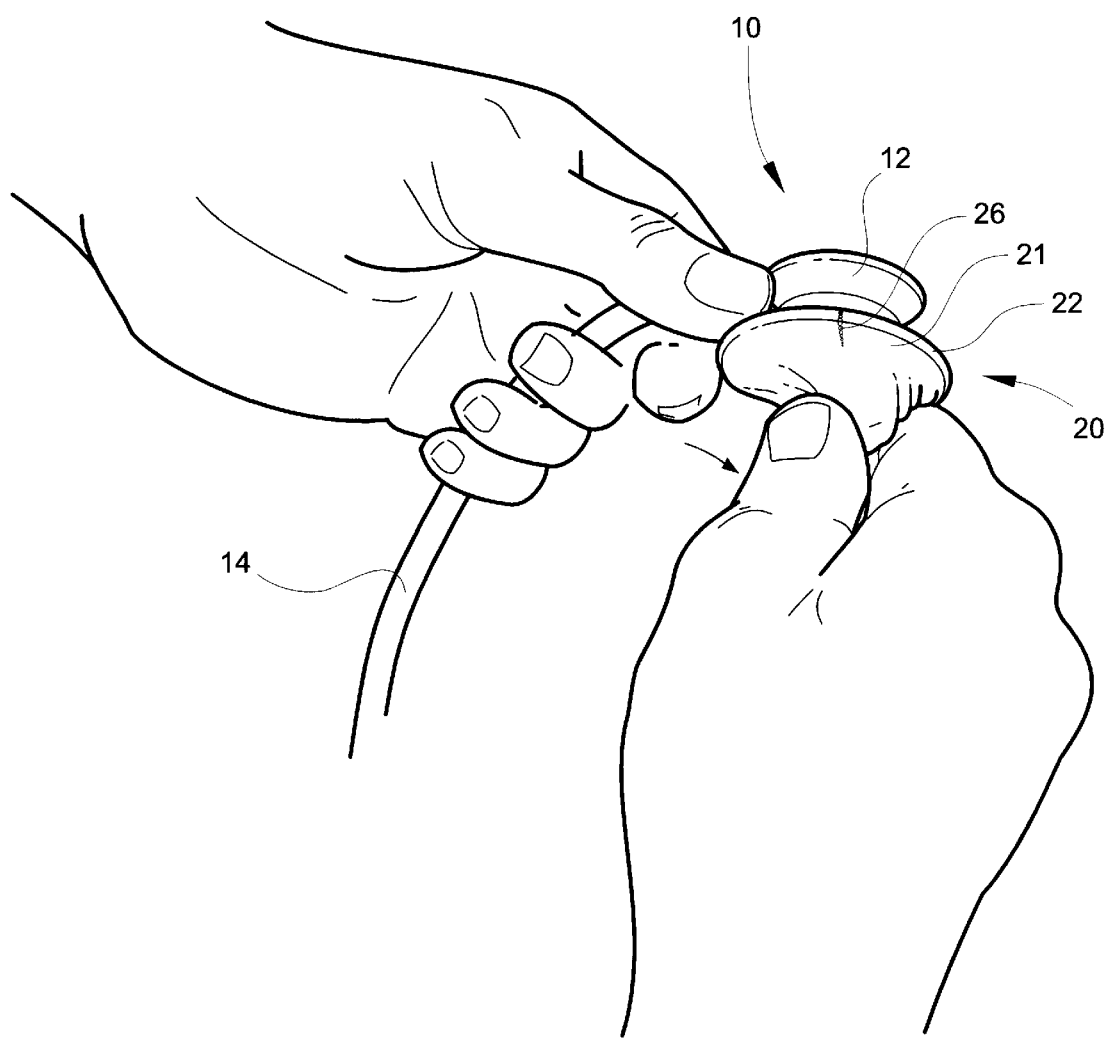
FIGS. 9A, 9B and 9C, 9D are two sets of sequential illustrations showing the removal of the stethoscope cover from the stethoscope.
Figure 9B:
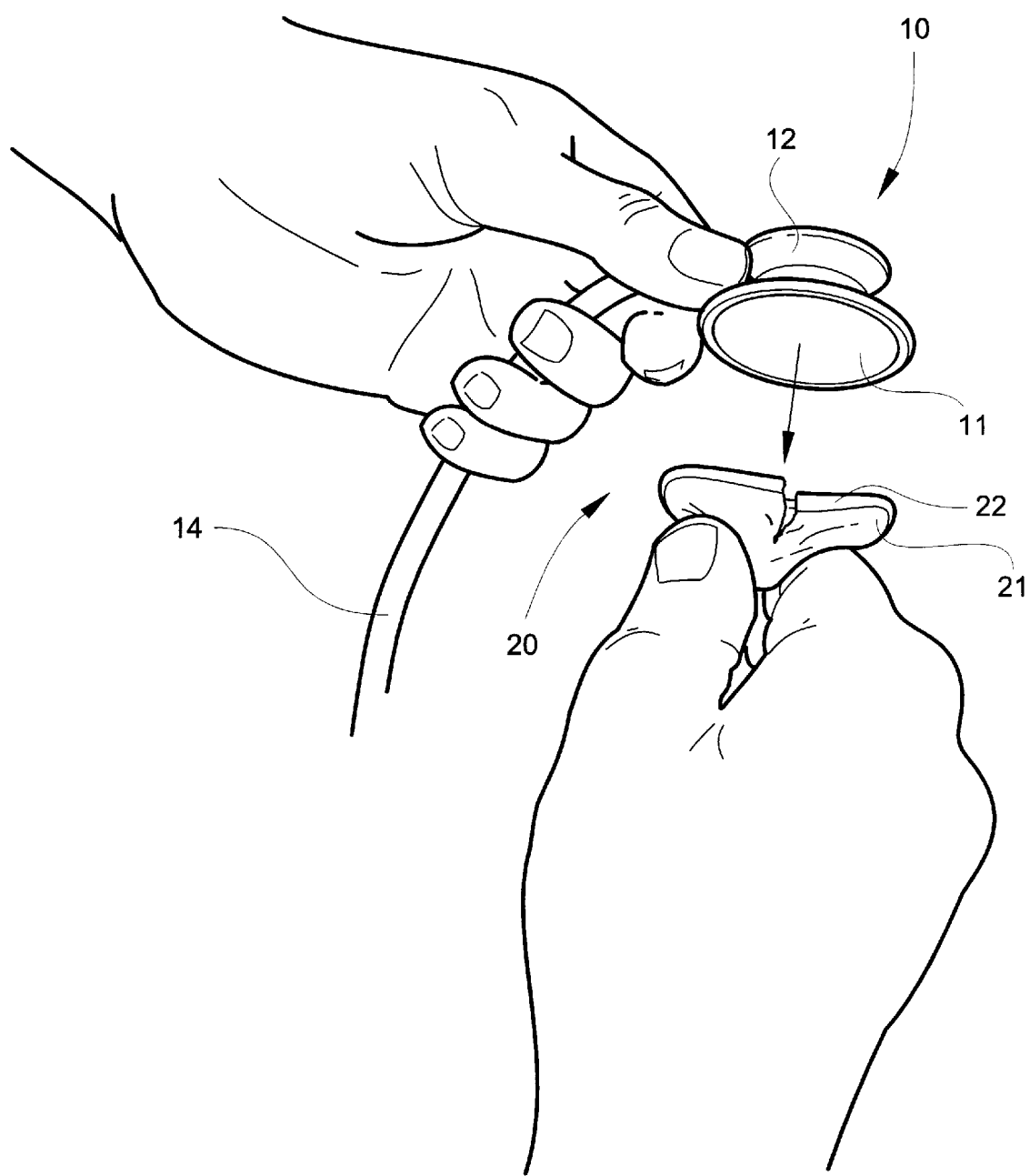
Figure 9C:
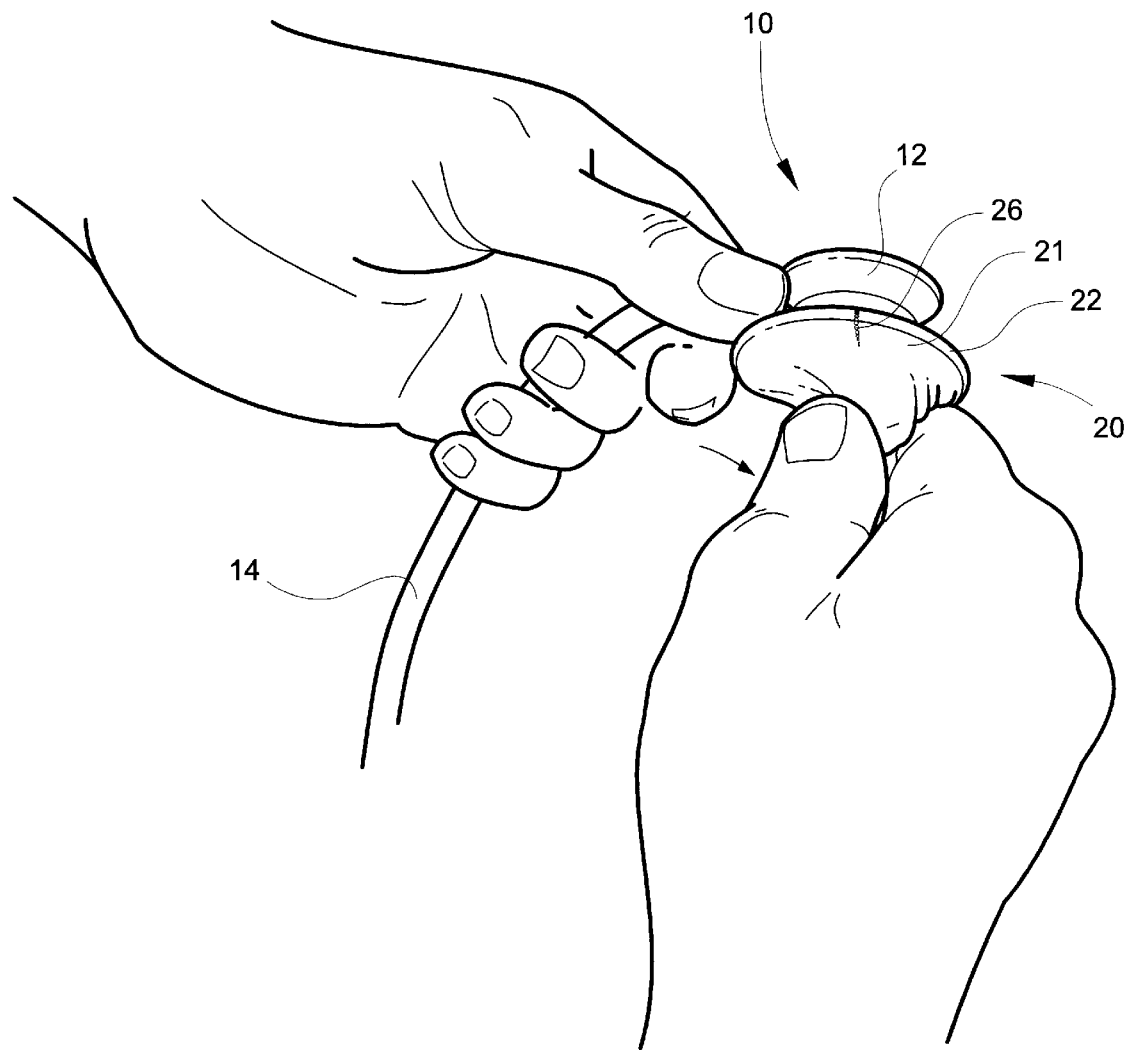
Figure 9D:
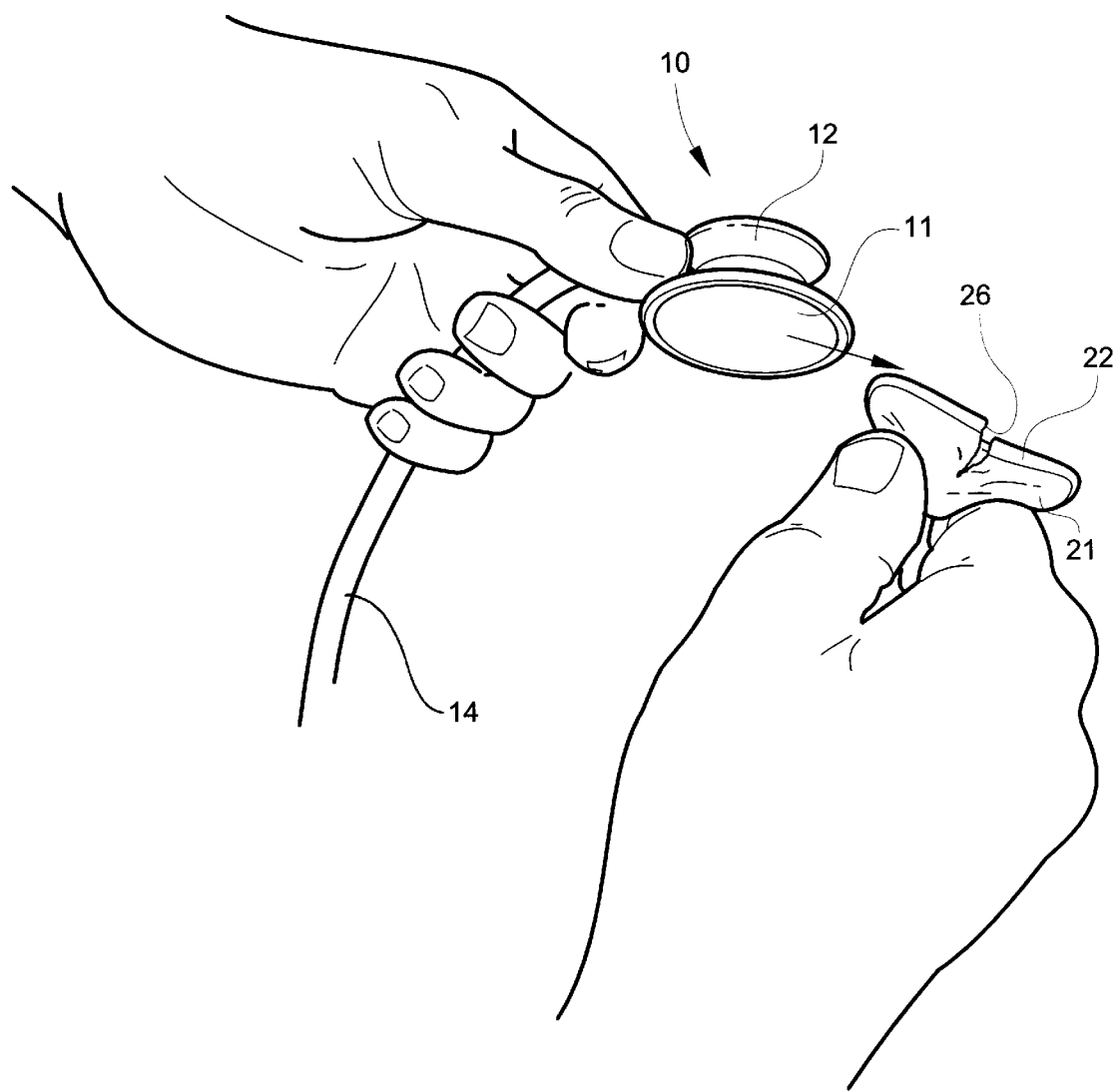

A single cover 20 is grasped in the hand and the rim 21 is placed over the edge of the diaphragm 12, as shown, or over the bell 11, as desired. The cover 20 is then stretched over the diaphragm 12 until the rim 21 surrounds the rim of the diaphragm 12. The cover 20 is then released, allowing it to snap into place over the diaphragm 12. As is shown in FIGS. 7 and 8, the cover 20 covers not only the face of the diaphragm 12 but also the side edge and the reverse side adjacent the side edge. Thus, any contamination which would otherwise contact these surfaces contact the disposable cover 20 instead.

Referring now to FIGS. 9A–9D, removal of the cover 20 is illustrated and explained. The cover 20 is grasped by pinching the dimple 24 between the thumb and the forefinger. The dimple 24 is stretched outwardly away from the stethoscope 10, FIG. 9A, to the point where the latex between the perforations 26 burst, tearing the rim of the cover 20, FIG. 9B. As is demonstrated in FIGS. 9C, 9D, the direction in which the dimple 24 is pulled in relation to the stethoscope 10 is unimportant.

The cover 20 may be autoclaved if necessary or desirable to enable the stethoscope to be used in a sterile environment. Insofar as is known, this has not heretofore been possible.

A disposable stethoscope cover is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A disposable cover for a stethoscope for being placed in a tensioned condition over and covering a patient-contacting portion of the stethoscope, said cover comprising:
   (a) an elastomeric material defining a disc-shaped body, wherein the depth of said body in the tensioned condition is substantially less than its diameter;
   (b) a raised rim integrally-formed with and surrounding the body; and
   (c) a raised dimple integrally-formed with and disposed centrally in the body for being grasped and pulled away from the stethoscope when removal of the cover from the stethoscope is desired.

2. A disposable cover for a stethoscope according to claim 1, wherein the diameter of said body is less than the diameter of the patient-contacting portion of the stethoscope.

3. A disposable cover for a stethoscope according to claim 1, wherein the cover includes a weakness area for being easily torn when the cover is stretched during removal of the cover from the stethoscope.

4. A disposable cover for a stethoscope according to claim 3, wherein the weakness area comprises a line of perforations in the rim of the cover.

5. A disposable cover for a stethoscope according to claim 3, wherein the weakness area comprises a line of axially-extending perforations in the rim of the cover.

6. A disposable cover for a stethoscope according to claim 3, wherein the weakness area comprises two lines of perforations in opposed circumferential sides of the rim of the cover.

7. A disposable cover for a stethoscope according to claim 1, wherein said elastomeric material is chosen from a group consisting of latex rubber, synthetic rubber, polyurethane and vinyl.

8. A disposable cover for a stethoscope for being placed in a tensioned condition over and covering a patient-contacting portion of the stethoscope, said cover comprising:
   (a) an elastomeric material defining a generally elliptical shaped body elongated along one axis, wherein the depth of said body in the tensioned condition is substantially less than its diameter;
   (b) a raised rim integrally-formed with and surrounding the body; and
   (c) a raised dimple integrally-formed with and disposed centrally in the body for being grasped and pulled away from the stethoscope when removal of the cover from the stethoscope is desired.

* * * * *